(12) United States Patent
Ding et al.

(10) Patent No.: US 11,731,920 B2
(45) Date of Patent: Aug. 22, 2023

(54) METHODS FOR CO-PRODUCING HYDROCARBON PRODUCTS AND AMMONIA

(71) Applicant: Battelle Energy Alliance, LLC, Idaho Falls, ID (US)

(72) Inventors: Dong Ding, Idaho Falls, ID (US); Wei Wu, Idaho Falls, ID (US); Hanping Ding, Idaho Falls, ID (US); Bin Hua, Ammon, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 216 days.

(21) Appl. No.: 16/532,276

(22) Filed: Aug. 5, 2019

(65) Prior Publication Data
US 2020/0039896 A1 Feb. 6, 2020

Related U.S. Application Data

(60) Provisional application No. 62/715,159, filed on Aug. 6, 2018.

(51) Int. Cl.
*C25B 1/02* (2006.01)
*C25B 1/27* (2021.01)
(Continued)

(52) U.S. Cl.
CPC ............ *C07C 2/24* (2013.01); *B01J 31/26* (2013.01); *C01C 1/0411* (2013.01); *C25B 1/27* (2021.01);
(Continued)

(58) Field of Classification Search
CPC .... C25B 1/27; C25B 3/23; C25B 3/25; C25B 3/29; C25D 1/02; C25D 3/03
(Continued)

(56) References Cited

U.S. PATENT DOCUMENTS 5,244,753 A * 9/1993 Taniguchi ........... H01M 8/1246
429/488
2008/0283411 A1* 11/2008 Eastman ............... F02M 25/12
205/343
(Continued)

FOREIGN PATENT DOCUMENTS

CN 103613105 A * 3/2014 ............... C01C 1/04

OTHER PUBLICATIONS

Wang et al., "Ammonia Synthesis at Atmospheric Pressure Using a Reactor with Thin Solid Electrolyte BaCe0.85Y0.15O3-α Membrane," Journal of Membrane Science (Sep. 15, 2010), vol. 360, Nos. 1-2, pp. 397-403. (Year: 2010).*
(Continued)

*Primary Examiner* — Edna Wong
(74) *Attorney, Agent, or Firm* — TraskBritt

(57) ABSTRACT

A method of a hydrocarbon product and ammonia comprises introducing $C_2H_6$ to a positive electrode of an electrochemical cell comprising the positive electrode, a negative electrode, and a proton-conducting membrane between the positive electrode and the negative electrode. The proton-conducting membrane comprising an electrolyte material having an ionic conductivity greater than or equal to about $10^{-2}$ S/cm at one or more temperatures within a range of from about 150° C. to about 600° C. $N_2$ is introduced to the negative electrode of the electrochemical cell. A potential difference is applied between the positive electrode and the negative electrode of the electrochemical cell. A system for co-producing higher hydrocarbons and NH3, and an electrochemical cell are also described.

15 Claims, 1 Drawing Sheet

(51) Int. Cl.
|  |  |
| --- | --- |
| *C25B 3/03* | (2021.01) |
| *C25B 3/23* | (2021.01) |
| *C07C 2/24* | (2006.01) |
| *B01J 31/26* | (2006.01) |
| *C01C 1/04* | (2006.01) |
| *C25B 9/19* | (2021.01) |
| *C25B 11/042* | (2021.01) |
| *C25B 11/046* | (2021.01) |
| *C25B 11/077* | (2021.01) |
| *C25B 13/04* | (2021.01) |
| *C25B 13/07* | (2021.01) |
| *C25B 9/23* | (2021.01) |

(52) U.S. Cl.
CPC .................. *C25B 3/03* (2021.01); *C25B 9/19* (2021.01); *C25B 9/23* (2021.01); *C25B 11/042* (2021.01); *C25B 11/046* (2021.01); *C25B 11/0773* (2021.01); *C25B 13/04* (2013.01); *C25B 13/07* (2021.01); *B01J 2231/20* (2013.01)

(58) Field of Classification Search
USPC .......................................... 205/462, 552, 637
See application file for complete search history.

(56) References Cited

U.S. PATENT DOCUMENTS

2014/0357904 A1* 12/2014 Teamey .................... C25B 3/25
204/252
2019/0284048 A1* 9/2019 Kjølseth .................. C25B 9/23

OTHER PUBLICATIONS

Shi et al., "Protonic Membrane for Fuel Cell for Co-Generation of Power and Ethylene," Journal of Power Sources (Jan. 21, 2008), vol. 176, No. 1, pp. 122-127. (Year: 2008).*
Kobayashi et al., "Electrochemical Synthesis of Ammonia Using Proton Conducting Solid Electrolyte and Ru-doped BaCe0.9Y0.1O3 -δ Electrode Catalyst," ECS Transactions (Jan. 11, 2017), vol. 75, No. 42, pp. 43-52. (Year: 2017).*
Amar et al., "Solid-State Electrochemical Synthesis of Ammonia: A Review," Journal of Solid State Electrochemistry (Sep. 1, 2011), vol. 15, No. 9, pp. 1845-1860. (Year: 2011).*
Kobayashi et al., "Electrochemical Synthesis of Ammonia Using Proton Conducting Solid Electrolyte and Ru-doped BaCe0.9Y0.1O3 -δ Electrode Catalyst," ECS Transactions (Jan. 11, 2017), vol. 75, No. 42, pp. 43-52. (Year: 2017).*
Goni-Urtiaga et al., "Solid Acids as Electrolyte Materials for Proton Exchange Membrane (PEM) Electrolysis," International Journal of Hydrogen Energy (Feb. 1, 2012), vol. 37, No. 4, pp. 3358-3372. (Year: 2012).*
Chen et al., "Performance on PBI/H3PO4 Proton Conducting Membrane Fuel Cell Using Ethane as Fuel," Chinese Journal of Inorganic Chemistry (Jan. 2010), vol. 26, No. 1, pp. 132-137. (Year: 2010).*
Kosaka et al., "Reaction Analysis of Electrochemical Synthesis of Ammonia with Proton Conducting BaCe0.9Y0.1O3 Solid Electrolyte," ECS Transactions (Jan. 5, 2017), vol. 75, No. 43, pp. 39-46. (Year: 2017).*

* cited by examiner

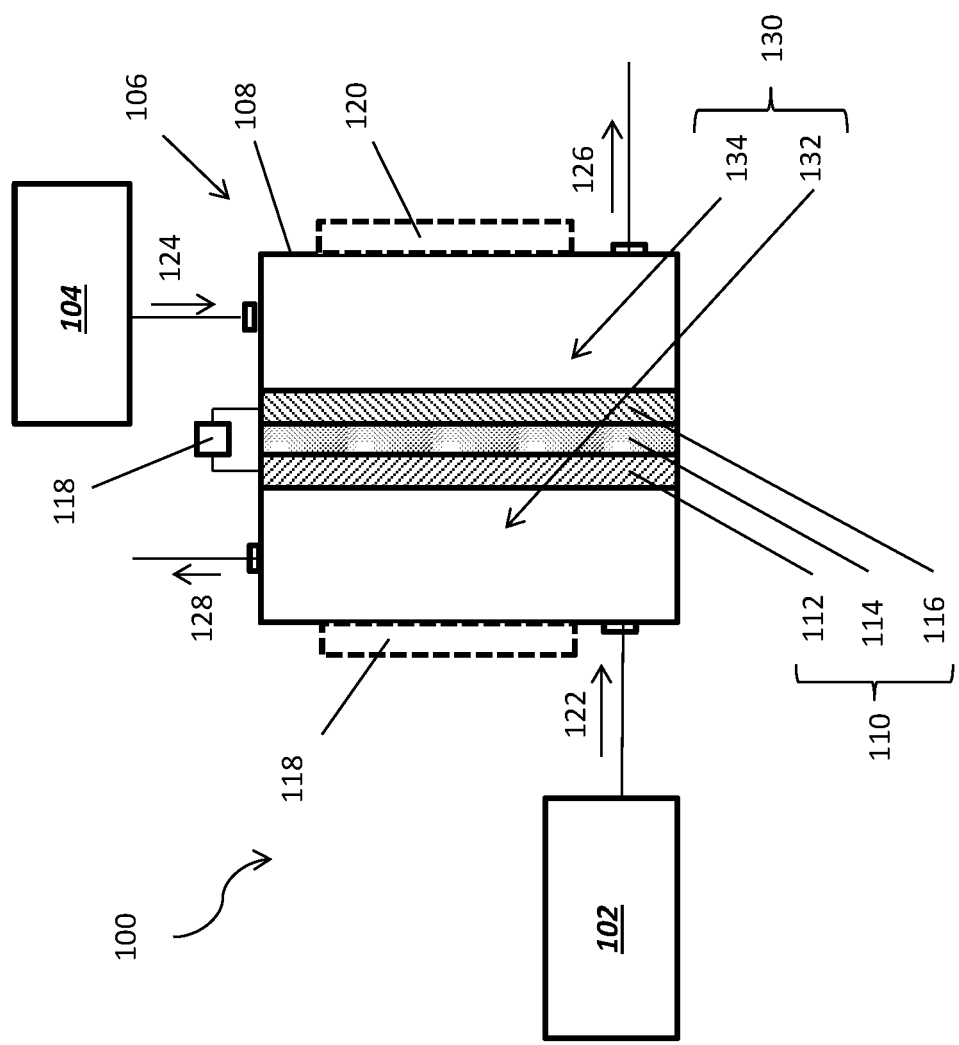

METHODS FOR CO-PRODUCING HYDROCARBON PRODUCTS AND AMMONIA

CROSS-REFERENCE TO RELATED APPLICATION

This application claims the benefit under 35 U.S.C. § 119(e) of U.S. Provisional Patent Application Ser. No. 62/715,159, filed Aug. 6, 2018, the disclosure of which is hereby incorporated herein in its entirety by this reference.

STATEMENT REGARDING FEDERALLY SPONSORED RESEARCH OR DEVELOPMENT

This invention was made government support under Contract Number DE-AC-07-05ID14517 awarded by the United States Department of Energy. The government has certain rights in the invention.

TECHNICAL FIELD

The disclosure, in various embodiments, relates to methods and systems for co-producing hydrocarbon products and ammonia through electrochemical activation of ethane, and to associated electrochemical cells.

BACKGROUND

Large reserves of natural gas continue to be discovered throughout the world, and have resulted in surpluses of ethane ($C_2H_6$) (i.e., the second major constituent of natural gas after methane ($CH_4$)). $C_2H_6$ is predominantly used to form ethylene ($C_2H_4$), a chemical feedstock for plastics (e.g., polyethylene) manufacturing, through conventional stream cracking processes. However, conventional stream cracking processes to convert $C_2H_6$ to $C_2H_4$ can require high temperatures (e.g., temperatures greater than or equal to about 850° C.) to activate $C_2H_6$, resulting in undesirable energy expenditures (e.g., thermal energy expenditures) and/or environmental impacts (e.g., greenhouse gas emissions effectuated by the energy needs of the stream cracking processes). Moreover, conventional stream cracking processes can require the use of complicated and costly systems and methods to purify (e.g., refine) the resulting ethylene product.

Ammonia ($NH_3$) is also a valued compound finding use in a wide variety of commercial and industrial applications. For example, $NH_3$ is commonly used as a precursor to various food, fertilizer, pharmaceutical, and cleaning products. However, conventional methods of producing $NH_3$ (e.g., the Haber-Bosch process) through nitrogen gas ($N_2$) hydrogenation are energy intensive, and can undesirably result in the production of significant amounts of greenhouse gases from combustion-based processes employed to generate the required energy.

It would be desirable to have new methods, systems, and apparatuses for synthesizing hydrocarbon products from $C_2H_6$. It would also be desirable if the new methods, systems, and apparatuses facilitated the production of hydrocarbons other than $C_2H_4$, and also facilitated the production (e.g., co-production) and isolation of $NH_3$. It would further be desirable if the new methods, systems, and apparatuses facilitated increased production efficiency, increased operational life, and were relatively inexpensive and simple in operation.

BRIEF SUMMARY

Embodiments described herein include methods, systems, and apparatuses for co-producing hydrocarbon products and $NH_3$ through electrochemical activation of $C_2H_6$. In accordance with one embodiment described herein, a method of forming a hydrocarbon product and $NH_3$ comprises introducing $C_2H_6$ to a positive electrode of an electrochemical cell comprising the positive electrode, a negative electrode, and a proton-conducting membrane between the positive electrode and the negative electrode. The proton-conducting membrane comprising an electrolyte material having an ionic conductivity greater than or equal to about $10^{-2}$ S/cm at one or more temperatures within a range of from about 150° C. to about 600° C. $N_2$ is introduced to the negative electrode of the electrochemical cell. A potential difference is applied between the positive electrode and the negative electrode of the electrochemical cell.

In additional embodiments, a system for co-producing hydrocarbon products and $NH_3$ comprises a source of $C_2H_6$, a source of $N_2$, and an electrochemical apparatus in fluid communication with the source of $C_2H_6$ and the source of $N_2$. The electrochemical apparatus comprises a housing structure, and an electrochemical cell within an internal chamber of the housing structure. The housing structure is configured and positioned to receive a $C_2H_6$ stream from the source of $C_2H_6$ and to receive a $N_2$ stream from the source of $N_2$. The electrochemical cell comprises a positive electrode, a negative electrode, and a proton-conducting membrane between the positive electrode and the negative electrode. The positive electrode comprising a catalyst material formulated to accelerate reaction rates to produce $C_2H_4$, $H^+$, and $e^-$ from $C_2H_6$, and to accelerate reaction rates to synthesize at least one hydrocarbon product from the produced $C_2H_4$. The negative electrode comprises another catalyst material formulated to accelerate reaction rates to produce $NH_3$ from $N_2$, $H^+$, and $e^-$. The proton-conducting membrane comprises an electrolyte material having an ionic conductivity greater than or equal to about $10^{-2}$ S/cm at one or more temperatures within a range of from about 150° C. to about 600° C.

In further embodiments, an electrochemical cell comprises a positive electrode, a negative electrode, and a proton-conducting membrane between the positive electrode and the negative electrode. The positive electrode comprises a first catalyst material formulated to accelerate to $C_2H_6$ deprotonation reaction rates to produce $C_2H_4$, $H^+$, and $e^-$ from $C_2H_6$, and to accelerate coupling reaction rates to synthesize at least one hydrocarbon product from the produced $C_2H_4$. The negative electrode comprises a second catalyst material formulated to accelerate $N_2$ protonation reaction rates to produce $NH_3$ from $N_2$, $H^+$, and $e^-$. The proton-conducting membrane comprises an electrolyte material having an ionic conductivity greater than or equal to about $10^{-2}$ S/cm at one or more temperatures within a range of from about 150° C. to about 600° C.

BRIEF DESCRIPTION OF THE DRAWINGS

FIG. 1 is a simplified schematic view of a system for co-producing hydrocarbon products and $NH_3$, in accordance with an embodiment of the disclosure.

DETAILED DESCRIPTION

Methods and systems for co-producing hydrocarbon products and $NH_3$ through electrochemical activation of $C_2H_6$ are disclosed. In some embodiments, a method of co-producing a hydrocarbon product (e.g., butylene, gasoline, diesel, etc.) and $NH_3$ comprises delivering $C_2H_6$ and $N_2$ to electrochemical apparatus including at least one electrochemical cell therein. The electrochemical cell includes a positive electrode (e.g., anode), a negative electrode (e.g., cathode), and a proton-conducting membrane between the positive electrode and the negative electrode. The positive electrode comprises at least one catalyst material formulated to accelerate to $C_2H_6$ deprotonation reaction rates to produce $C_2H_4$, $H^+$, and $e^-$ from $C_2H_6$, and to accelerate ethyl coupling reaction rates to synthesize at least one hydrocarbon product from the produced $C_2H_4$. The negative electrode comprises at least one additional catalyst material formulated to accelerate $N_2$ protonation reaction rates to produce $NH_3$ from $N_2$, $H^+$, and $e^-$. The proton-conducting membrane comprises an electrolyte material having an ionic conductivity greater than or equal to about $10^{-2}$ S/cm at one or more temperatures within a range of from about 150° C. to about 600° C. The $C_2H_6$ is introduced to the positive electrode of the electrochemical cell, the $N_2$ is introduced to the negative electrode of the electrochemical cell, and a potential difference is applied between the positive electrode and the negative electrode of the electrochemical cell to produce the hydrocarbon product and the $NH_3$. The methods, systems, and apparatuses of the disclosure may be more efficient (e.g., increasing higher hydrocarbon and $NH_3$ production efficiency; reducing equipment, material, and/or energy requirements; etc.), more durable, and/or less complicated as compared to conventional methods, conventional systems, and conventional apparatuses for producing one or more of higher hydrocarbons and $NH_3$.

The following description provides specific details, such as material compositions and processing conditions (e.g., temperatures, pressures, flow rates, etc.) in order to provide a thorough description of embodiments of the disclosure. However, a person of ordinary skill in the art will understand that the embodiments of the disclosure may be practiced without necessarily employing these specific details. Indeed, the embodiments of the disclosure may be practiced in conjunction with conventional systems and methods employed in the industry. In addition, only those process components and acts necessary to understand the embodiments of the present disclosure are described in detail below. A person of ordinary skill in the art will understand that some process components (e.g., pipelines, line filters, valves, temperature detectors, flow detectors, pressure detectors, and the like) are inherently disclosed herein and that adding various conventional process components and acts would be in accord with the disclosure. In addition, the drawings accompanying the application are for illustrative purposes only, and are not meant to be actual views of any particular material, device, or system.

As used herein, the term "lower hydrocarbon" means and includes an aliphatic hydrocarbon having from one carbon atom to four carbon atoms (e.g., methane, ethane, ethylene, acetylene, propane, propylene, n-butane, isobutene, butane, isobutene, etc.).

As used herein, the terms "higher hydrocarbon" and "hydrocarbon product" mean and include an aliphatic or cyclic hydrocarbon having at least one more carbon atom than a lower hydrocarbon used to form the higher hydrocarbon.

As used herein, the term "cyclic hydrocarbon" means and includes at least one closed ring hydrocarbon, such as an alicyclic hydrocarbon, an aromatic hydrocarbon, or a combination thereof. The cyclic hydrocarbon may include only carbon and hydrogen, or may include carbon, hydrogen, and at least one heteroatom.

As used herein, the term "heteroatom" means and includes an element other than carbon and hydrogen, such as oxygen (O), nitrogen (N), or sulfur (S).

As used herein, the terms "catalyst material" and "catalyst" each mean and include a material formulated to promote one or more reactions, resulting in the formation of a product.

As used herein, the term "negative electrode" means and includes an electrode having a relatively lower electrode potential in an electrochemical cell (i.e., lower than the electrode potential in a positive electrode therein). Conversely, as used herein, the term "positive electrode" means and includes an electrode having a relatively higher electrode potential in an electrochemical cell (i.e., higher than the electrode potential in a negative electrode therein).

As used herein the term "electrolyte" means and includes an ionic conductor, which can be in a solid state, a liquid state, or a gas state (e.g., plasma).

As used herein, the term "compatible" means that a material does not undesirably react, decompose, or absorb another material, and also that the material does not undesirably impair the chemical and/or mechanical properties of the another material.

As used herein, spatially relative terms, such as "beneath," "below," "lower," "bottom," "above," "upper," "top," "front," "rear," "left," "right," and the like, may be used for ease of description to describe one element's or feature's relationship to another element(s) or feature(s) as illustrated in the figures. Unless otherwise specified, the spatially relative terms are intended to encompass different orientations of the materials in addition to the orientation depicted in the figures. For example, if materials in the figures are inverted, elements described as "below" or "beneath" or "under" or "on bottom of" other elements or features would then be oriented "above" or "on top of" the other elements or features. Thus, the term "below" can encompass both an orientation of above and below, depending on the context in which the term is used, which will be evident to one of ordinary skill in the art. The materials may be otherwise oriented (e.g., rotated 90 degrees, inverted, flipped) and the spatially relative descriptors used herein interpreted accordingly.

As used herein, the singular forms "a," "an," and "the" are intended to include the plural forms as well, unless the context clearly indicates otherwise.

As used herein, "and/or" includes any and all combinations of one or more of the associated listed items.

As used herein, the term "configured" refers to a size, shape, material composition, material distribution, and arrangement of one or more of at least one structure and at least one apparatus facilitating operation of one or more of the structure and the apparatus in a pre-determined way.

As used herein, the term "substantially" in reference to a given parameter, property, or condition means and includes to a degree that one of ordinary skill in the art would understand that the given parameter, property, or condition is met with a degree of variance, such as within acceptable manufacturing tolerances. By way of example, depending on the particular parameter, property, or condition that is substantially met, the parameter, property, or condition may be at least 90.0% met, at least 95.0% met, at least 99.0% met, at least 99.9% met, or even 100.0% met.

As used herein, "about" or "approximately" in reference to a numerical value for a particular parameter is inclusive of the numerical value and a degree of variance from the numerical value that one of ordinary skill in the art would understand is within acceptable tolerances for the particular parameter. For example, "about" or "approximately" in reference to a numerical value may include additional numerical values within a range of from 90.0 percent to 110.0 percent of the numerical value, such as within a range of from 95.0 percent to 105.0 percent of the numerical value, within a range of from 97.5 percent to 102.5 percent of the numerical value, within a range of from 99.0 percent to 101.0 percent of the numerical value, within a range of from 99.5 percent to 100.5 percent of the numerical value, or within a range of from 99.9 percent to 100.1 percent of the numerical value.

An embodiment of the disclosure will now be described with reference to FIG. 1, which schematically illustrates a system 100 (e.g., $C_2H_6$ activation system) for co-producing hydrocarbon products and $NH_3$. The system 100 may be used to convert $C_2H_6$ and $N_2$ into at least one higher hydrocarbon (e.g., butylene, gasoline, diesel, etc.) and $NH_3$. As shown in FIG. 1, the system 100 may include at least one $C_2H_6$ source 102 (e.g., containment vessel), at least one $N_2$ source 104 (e.g., containment vessel), and at least one electrochemical apparatus 106 in fluid communication with each of the $C_2H_6$ source 102 and the $N_2$ source 104. The electrochemical apparatus 106 includes a housing structure 108, and at least one electrochemical cell 110 contained within the housing structure 108. The electrochemical cell 110 is electrically connected (e.g., coupled) to a power source 118, and includes a positive electrode 112 (e.g. anode), a negative electrode 116 (e.g., cathode), and a proton-conducting membrane 114 between the positive electrode 112 and the negative electrode 116. As shown in FIG. 1, optionally, the system 100 may also include at least one heating apparatus 120 operatively associated with the electrochemical apparatus 106.

During use and operation, the system 100 directs a $C_2H_6$ stream 122 into the electrochemical apparatus 106 to interact with the positive electrode 112 of the electrochemical cell 110. A potential difference (e.g., voltage) is applied between the positive electrode 112 and the negative electrode 116 of the electrochemical cell 110 by the power source 118 so that as the $C_2H_6$ interacts with the positive electrode 112, H atoms of the $C_2H_6$ release their electrons ($e^-$) to generate ethylene ($C_2H_4$), hydrogen ions ($H^+$) (i.e., protons), and electrons ($e^-$) through non-oxidative deprotonation according to the following equation:

$$C_2H_6 \rightarrow C_2H_4 + 2H^+ + 2e^- \quad (1).$$

The generated $H^+$ permeate (e.g., diffuse) across the proton-conducting membrane 114 to the negative electrode 116, the generated $e^-$ are directed to the power source 118 through external circuitry. At the negative electrode 116, the generated $H^+$ exiting the proton-conducting membrane 114 react with $N_2$ delivered into the electrochemical apparatus 106 from an $N_2$ stream 124 directed from the $N_2$ source 104 and $e^-$ received from the power source 118 in the presence of a catalyst material of the negative electrode 116 to produce $NH_3$, according to the following equation:

$$N_2 \xrightarrow{3H^+, 3e^-} NH_3 \quad (2)$$

Unlike conventional methods (e.g., the Haber-Bosch process) of forming $NH_3$ that react $N_2$ with hydrogen gas ($H_2$), the system 100 directly reacts $H^+$ with the $N_2$ to form $NH_3$. Accordingly, the formation of $NH_3$ at the negative electrode 116 is not constrained (e.g., limited) by the previous formation of $H_2$ through a hydrogen evolution reaction (HER). In addition, the $N_2$ reduction reaction occurs at reduced pressures (e.g., ambient pressure) relative to conventional catalytic hydrogenation methods. The produced $NH_3$ exits the electrochemical apparatus 106 as a $NH_3$ stream 126. At the positive electrode 112, the produced $C_2H_4$ may undergo at least one ethyl coupling reaction (ECR) in the presence of a catalyst material of the positive electrode 112 to synthesize at least one hydrocarbon product (e.g., higher hydrocarbon), according to the following equation:

$$nC_2H_4 \rightarrow C_{2n}H_{4n} \quad (2).$$

The hydrocarbon product may then exit the electrochemical apparatus 106 as a hydrocarbon product stream 128.

As described in further detail below, the hydrocarbon products synthesized at the positive electrode 112 and the production of $NH_3$ at the negative electrode 116 may at least partially depend on the material compositions and flow rates of the $C_2H_6$ stream 122 and the $N_2$ stream 124; the configuration (e.g., size, shape, material composition, material distribution, arrangement) of the positive electrode 112, including the types, quantities, distribution, and properties (e.g., geometric properties, thermodynamic properties, etc.) of catalyst materials thereof promoting $C_2H_6$ deprotonation reactions and/or ethyl coupling reactions; the configuration of the proton-conducting membrane 114, and the impact thereof on the diffusivity (e.g., diffusion rate) of generated $H^+$ therethrough; the configuration of the negative electrode 116, including the types, quantities, and properties (e.g., geometric properties, thermodynamic properties, etc.) of catalyst materials thereof; and the operational parameters (e.g., temperatures, pressures, etc.) of the electrochemical apparatus 106. Such operational factors may be controlled (e.g., adjusted, maintained, etc.) as desired to control the types, quantities, and rate of production of the hydrocarbon product(s) synthesized at the positive electrode 112 and to control the quantity and rate of production of the $NH_3$ produced at the negative electrode 116. In some embodiments, the hydrocarbon product(s) exiting the electrochemical apparatus 106 in the hydrocarbon product stream 128 may be examined (e.g., through in-line gas chromatography-mass spectrometry (GS-MS)) and compared to a mathematically modeled Anderson-Schulz-Flory distribution to analyze whether or not sufficient ethyl coupling reactions are occurring at the positive electrode 112 for the synthesis of one or more desired higher hydrocarbons. One or more operational factors of the system 100 (e.g., one or more of the type, quantity, and distribution of catalyst material(s) in the positive electrode 112, the operating temperature of the electrochemical apparatus 106, etc.) may be adjusted or maintained based on the results of the analysis. Accordingly, the operational factors of the system 100 may be tailored to facilitate the co-production of $NH_3$ and one or more specific higher hydrocarbons from the components of the $C_2H_6$ stream 122 and the $N_2$ stream 124.

The $C_2H_6$ stream 122 may be formed of and include $C_2H_6$. In addition, the $C_2H_6$ stream 122 may, optionally, include one or more other materials (e.g., molecules), such as one or more other lower hydrocarbons (e.g., one or more other $C_1$ to $C_4$ hydrocarbons, such as one or more of $CH_4$, propane, and butane) that may undergo a chemical reaction in the presence of the positive electrode 112 of the electrochemical cell 110 to produce at least one higher hydrocarbon, and/or one or more other materials (e.g., $H_2$, $N_2$, etc.).

In some embodiments, the $C_2H_6$ stream 122 is substantially free of materials other than $C_2H_6$. In additional embodiments, the $C_2H_6$ stream 122 includes $C_2H_6$ and $CH_4$. The $C_2H_6$ stream 122 may be substantially gaseous (e.g., may only include a single gaseous phase), may be substantially liquid (e.g., may only include a single liquid phase), or may include a combination of liquid and gaseous phases. The phase(s) of the $C_2H_6$ stream 122 (and, hence, a temperature and a pressure of the $C_2H_6$ stream 122) may at least partially depend on the operating temperature of the electrochemical cell 110 of the electrochemical apparatus 106. In some embodiments, the $C_2H_6$ stream 122 is substantially gaseous.

A single (e.g., only one) $C_2H_6$ stream 122 may be directed into the electrochemical apparatus 106 from the $C_2H_6$ source 102, or multiple (e.g., more than one) $C_2H_6$ streams 120 may be directed into the electrochemical apparatus 106 from the $C_2H_6$ source 102. If multiple $C_2H_6$ streams 120 are directed into the electrochemical apparatus 106, each of the multiple $C_2H_6$ streams 120 may exhibit substantially the same properties (e.g., substantially the same material composition, substantially the same temperature, substantially the same pressure, substantially the same flow rate, etc.), or at least one of the multiple $C_2H_6$ streams exhibit one or more different properties (e.g., a different material composition, a different temperature, a different pressure, a different flow rate, etc.) than at least one other of the multiple $C_2H_6$ streams 120.

The $N_2$ stream 124 entering the electrochemical apparatus 106 may be formed of and include $N_2$. The $N_2$ may be present in the $N_2$ stream 124 in one or more of gaseous phase and a liquid phase. The phase(s) of the $N_2$ (and, hence, a temperature and a pressure of the $N_2$ stream 124) may at least partially depend on the operating temperature of the electrochemical cell 110 of the electrochemical apparatus 106. For example, at operating temperatures less than or equal to about 250° C. (e.g., within a range of from about 150° C. to about 250° C.), the $N_2$ may be present in the $N_2$ stream 124 in a liquid phase, a gaseous phase, or combination thereof. As another example, at operating temperatures greater than about 250° C. (e.g., greater than about 250° C. and less than or equal to about 650°, the $N_2$ may be present in the $N_2$ stream 124 in a gaseous phase. The $N_2$ stream 124 may only include $N_2$, or may include $N_2$ and one or more other materials. In some embodiments, the $N_2$ stream 124 is substantially free of materials other than $N_2$. One or more apparatuses (e.g., heat exchangers, pumps, compressors, expanders, mass flow control devices, etc.) may be employed within the system 100 to adjust the one or more of the temperature, pressure, and flow rate of the $N_2$ stream 124 delivered into the electrochemical apparatus 106.

A single (e.g., only one) $N_2$ stream 124 may be directed into the electrochemical apparatus 106, or multiple (e.g., more than one) $N_2$ streams 124 may be directed into the electrochemical apparatus 106. If multiple $N_2$ streams 124 are directed into the electrochemical apparatus 106, each of the multiple $N_2$ streams 124 may exhibit substantially the same properties (e.g., substantially the same material composition, substantially the same temperature, substantially the same pressure, substantially the same flow rate, etc.), or at least one of the multiple $N_2$ streams 124 may exhibit one or more different properties (e.g., a different material composition, a different temperature, a different pressure, a different flow rate, etc.) than at least one other of the multiple $N_2$ streams 124.

The heating apparatus 120, if present, may comprise at least one apparatus (e.g., one or more of a combustion heater, an electrical resistance heater, an inductive heater, and an electromagnetic heater) configured and operated to heat one or more of the gaseous $C_2H_6$ stream 122, the $N_2$ stream 124, and at least a portion of the electrochemical apparatus 106 to an operating temperature of the electrochemical apparatus 106. The operating temperature of the electrochemical apparatus 106 may at least partially depend on a material composition of the proton-conducting membrane 114 of the electrochemical cell 110 thereof, as described in further detail below. In some embodiments, the heating apparatus 120 heats one or more of the $C_2H_6$ stream 122, the $N_2$ stream 124, and at least a portion of the electrochemical apparatus 106 to a temperature within a range of from about 150° C. to about 650° C. In additional embodiments, such as in embodiments wherein a temperature of the $C_2H_6$ stream 122 is already within the operating temperature range of the electrochemical cell 110 of the electrochemical apparatus 106, the heating apparatus 120 may be omitted (e.g., absent) from the system 100.

With continued reference to FIG. 1, the electrochemical apparatus 106, including the housing structure 108 and the electrochemical cell 110 thereof, is configured and operated to form the $NH_3$ stream 126 and the hydrocarbon product stream 128 from the $C_2H_6$ stream 122 and the $N_2$ stream 124 according to the reactions of Equations (1) through (3) above. The housing structure 108 may exhibit any shape (e.g., a tubular shape, a quadrilateral shape, a spherical shape, a semi-spherical shape, a cylindrical shape, a semi-cylindrical shape, truncated versions thereof, or an irregular shape) and size able to contain (e.g., hold) the electrochemical cell 110 therein, to receive and direct the $C_2H_6$ stream 122 to the positive electrode 112 of the electrochemical cell 110, to direct the high hydrocarbon product(s) synthesized at the positive electrode 112 away from the electrochemical apparatus 106 as the hydrocarbon product stream 128, and to direct the $NH_3$ formed at the negative electrode 116 of the electrochemical cell 110 away from the electrochemical apparatus 106 as the $NH_3$ stream 126. In addition, the housing structure 108 may be formed of and include any material (e.g., glass, metal, alloy, polymer, ceramic, composite, combination thereof, etc.) compatible with the operating conditions (e.g., temperatures, pressures, etc.) of the electrochemical apparatus 106.

The housing structure 108 may at least partially define at least one internal chamber 130 at least partially surrounding the electrochemical cell 110. The electrochemical cell 110 may serve as a boundary between a first region 132 (e.g., an anodic region) of the internal chamber 130 configured and positioned to receive the $C_2H_6$ stream 122 and to direct the hydrocarbon product stream 128 from the electrochemical apparatus 106, and a second region 134 (e.g., a cathodic region) of the internal chamber 130 configured and positioned to receive the $NH_3$ produced at the negative electrode 116 of the electrochemical cell 110. Molecules (e.g., $C_2H_6$) of the $C_2H_6$ stream 122 may be substantially limited to the first region 132 of the internal chamber 130 by the configurations and positions of the housing structure 108 and the electrochemical cell 110. Keeping the second region 134 of the internal chamber 130 substantially free of molecules from the $C_2H_6$ stream 122 circumvents additional processing of the produced $NH_3$ (e.g., to separate the produced $NH_3$ from $C_2H_6$) that may otherwise be necessary if the components of the $C_2H_6$ stream 122 were also delivered to within the second region 134 of the internal chamber 130.

As shown in FIG. 1, the positive electrode 112 and the negative electrode 116 of the electrochemical cell 110 are electrically coupled to the power source 118, and the proton-conducting membrane 114 is disposed on and between the positive electrode 112 and the negative electrode 116. The proton-conducting membrane 114 is configured and formulated to conduct $H^+$ from the positive electrode 112 to the negative electrode 116, while electrically insulating the negative electrode 116 from the positive electrode 112 and preventing the migration of gaseous materials therethrough. Electrons generated at the positive electrode 112 through the reaction of Equation (1) described above may, for example, flow from the positive electrode 112 into a negative current collector, through the power source 118 and a positive electrode current collector, and into negative electrode 116 to facilitate the protonation of $N_2$ at the negative electrode 116 to form $NH_3$ through the reaction of Equation (2) described above.

The proton-conducting membrane 114 may be formed of and include at least one electrolyte material exhibiting an ionic conductivity (e.g., $H^+$ conductivity) greater than or equal to about $10^{-2}$ S/cm (e.g., within a range of from about $10^{-2}$ S/cm to about 1 S/cm) at one or more temperatures within a range of from about 150° C. to about 650° C. (e.g., from about 200° C. to about 600° C., from about 300° C. to about 500° C.). In addition, the electrolyte material may be formulated to remain substantially adhered (e.g., laminated) to the positive electrode 112 and the negative electrode 116 at relatively high current densities, such as at current densities greater than or equal to about 0.1 amperes per square centimeter ($A/cm^2$) (e.g., greater than or equal to about 0.5 $A/cm^2$, greater than or equal to about 1.0 $A/cm^2$, greater than or equal to about 2.0 $A/cm^2$, etc.). For example, the proton-conducting membrane 114 may comprise one or more of a perovskite material, a solid acid material, and a polybenzimidazole (PBI) material. The material composition of the proton-conducting membrane 114 may provide the proton-conducting membrane 114 with enhanced ionic conductivity at a temperature within the range of from about 150° C. to about 650° C. as compared to conventional membranes (e.g., membranes employing conventional electrolyte materials, such as yttria-stabilized zirconia (YSZ)) of conventional electrolysis cells. By way of non-limiting example, the electrolyte material (e.g., perovskite material, solid acid material, PBI material) of the proton-conducting membrane 114 may have orders of magnitude higher ionic conductivity than YSZ at operational temperatures thereof within the range of from about 150° C. to about 650° C.

In some embodiments, the proton-conducting membrane 114 is formed of and includes at least one perovskite material having an operational temperature (e.g., a temperature at which the $H^+$ conductivity of the perovskite material is greater than or equal to about $10^{-2}$ S/cm, such as within a range of from about $10^{-2}$ S/cm to about $10^{-1}$ S/cm) within a range of from about 350° C. to about 650° C. By way of non-limiting example, the proton-conducting membrane 114 may comprise one or more of a yttrium- and ytterbium-doped barium-zirconate-cerate (BZCYYb), such as $BaZr_{0.8-y}Ce_yY_{0.2-x}Yb_xO_{3-\delta}$, wherein x and y are dopant levels and $\delta$ is the oxygen deficit (e.g., $BaZr_{0.3}Ce_{0.5}Y_{0.1}O_{3-\delta}$); a yttrium- and ytterbium-doped barium-strontium-niobate (BSNYYb), such as $Ba_3(Sr_{1-x}Nb_{2-y}Y_xYb_y)O_{9-\delta}$, wherein x and y are dopant levels and $\delta$ is the oxygen deficit; doped barium-cerate ($BaCeO_3$) (e.g., yttrium-doped $BaCeO_3$ (BCY)); doped barium-zirconate ($BaZrO_3$) (e.g., yttrium-doped $BaCeO_3$ (BZY)); barium-yttrium-stannate ($Ba_2(YSn)O_{5.5}$); and barium-calcium-niobate ($Ba_3(CaNb_2)O_9$). In some embodiments, the proton-conducting membrane 114 comprises BZCYYb.

In further embodiments, the proton-conducting membrane 114 is formed of and includes at least one solid acid material having an operational temperature (e.g., a temperature at which the $H^+$ conductivity of the solid acid material is greater than or equal to about $10^{-2}$ S/cm, such as within a range of from about $10^{-2}$ S/cm to about 1 S/cm) within a range of from about 200° C. to about 400° C. By way of non-limiting example, the proton-conducting membrane 114 may comprise a solid acid phosphate material, such as solid acid cesium dihydrogen phosphate ($CsH_2PO_4$). The solid acid material may be doped (e.g., doped $CsH_2PO_4$), or may be undoped (e.g., undoped $CsH_2PO_4$). In some embodiments, the proton-conducting membrane 114 comprises $CsH_2PO_4$.

In additional embodiments, the proton-conducting membrane 114 is formed of and includes at least one PBI material having an operational temperature (e.g., a temperature at which the $H^+$ conductivity of the PBI material is greater than or equal to about $10^{-2}$ S/cm, such as within a range of from about $10^{-2}$ S/cm to about 1 S/cm) within a range of from about 150° C. to about 250° C. By way of non-limiting example, the proton-conducting membrane 114 may comprise a doped PBI, such as phosphoric acid ($H_3PO_4$) doped PBI. In some embodiments, the proton-conducting membrane 114 comprises $H_3PO_4$-doped PBI.

The proton-conducting membrane 114 may be substantially homogeneous or may be substantially heterogeneous. As used herein, the term "homogeneous" means amounts of a material do not vary throughout different portions (e.g., different lateral and longitudinal portions) of a structure. Conversely, as used herein, the term "heterogeneous" means amounts of a material vary throughout different portions of a structure. Amounts of the material may vary stepwise (e.g., change abruptly), or may vary continuously (e.g., change progressively, such as linearly, parabolically) throughout different portions of the structure. In some embodiments, the proton-conducting membrane 114 is substantially homogeneous. In additional embodiments, the proton-conducting membrane 114 is heterogeneous. The proton-conducting membrane 114 may, for example, be formed of and include a stack of at least two (e.g., at least three, at least four, etc.) different materials. As a non-limiting example, the proton-conducting membrane 114 may comprise a stack of at least two (e.g., at least three, at least four, etc.) different perovskite materials individually having an operational temperature within a range of from about 350° C. to about 650° C. As another non-limiting example, the proton-conducting membrane 114 may comprise a stack of at least two (e.g., at least three, at least four, etc.) different solid acid materials individually having an operational temperature within a range of from about 200° C. to about 400° C. As a further non-limiting example, the proton-conducting membrane 114 may comprise a stack of at least two (e.g., at least three, at least four, etc.) different PBI materials individually having an operational temperature within a range of from about 150° C. to about 250° C.

The proton-conducting membrane 114 may exhibit any desired dimensions (e.g., length, width, thickness) and any desired shape (e.g., a cubic shape, cuboidal shape, a tubular shape, a tubular spiral shape, a spherical shape, a semi-spherical shape, a cylindrical shape, a semi-cylindrical shape, a conical shape, a triangular prismatic shape, a truncated version of one or more of the foregoing, and irregular shape). The dimensions and the shape of the proton-conducting membrane 114 may be selected such that the proton-conducting membrane 114 substantially intervenes between opposing surfaces of the positive electrode 112 and the negative electrode 116, and exhibits an $H^+$ conductivity greater than or equal to about $10^{-2}$ S/cm (e.g., from about $10^{-2}$ S/cm to about 1 S/cm) at a temperature within a range of from about 150° C. to about 650° C. A thickness of the proton-conducting membrane 114 may be within a range of from about 5 micrometers (μm) to about 1000 μm, and may at least partially depend on the material composition of the proton-conducting membrane 114. For example, a proton-conducting membrane 114 formed of and including at least one perovskite material may have a thickness with a range of from about 5 μm to about 1000 μm; a proton-conducting membrane 114 formed of and including at least one solid acid material may have a thickness with a range of from about 5 μm to about 1000 μm; and a proton-conducting membrane 114 formed of and including at least one PBI material may have a thickness with a range of from about 50 μm to about 1000 μm.

The positive electrode 112 and the negative electrode 116 may individually be formed of and include at least one catalyst-doped material compatible with the material composition of the proton-conducting membrane 114 and the operating conditions (e.g., temperature, pressure, current density, etc.) of the electrochemical cell 110, and facilitating the formation of the $NH_3$ stream 126 and hydrocarbon product stream 128 from the $C_2H_6$ stream 122 and the $N_2$ stream 124 at an operational temperature within the range of from about 150° C. to about 600° C. Accordingly, the material compositions of the positive electrode 112 and the negative electrode 116 may be selected relative to one another, the material composition of the proton-conducting membrane 114, the material composition of the $CH_4$ stream 122, and the operating conditions of the electrochemical cell 110.

The catalyst-doped materials of the positive electrode 112 includes at least one catalyst material thereon, thereover, and/or therein that accelerates reaction rates at the positive electrode 112 to produce $C_2H_4$, $H^+$, and $e^-$ from $C_2H_6$ in accordance with Equation (1) above, and that also accelerates reaction rates at the positive electrode 112 to synthesize one or more higher hydrocarbons from the produced $C_2H_4$ in accordance with Equation (3) above. The catalyst material of the positive electrode 112 may, for example, comprise a metallic material (e.g., a metal, an alloy, a composite of two or more metals and/or alloys) formulated to accelerate reaction rates at the positive electrode 112 to produce $C_2H_4$, $H^+$, and $e^-$ from $C_2H_6$, and to accelerate reaction rates for the synthesis of higher hydrocarbons from the produced $C_2H_4$.

The catalyst material of the positive electrode 112 may comprise a single (e.g., only one) element (e.g., a single metal), or may comprise multiple (e.g., more than one) elements (e.g., multiple metals). The catalyst material of the positive electrode 112 may comprise one or more of elemental particles, alloy particles, and composite particles. In some embodiments, the catalyst material of the positive electrode 112 comprises elemental particles of a first metal formulated to accelerate reaction rates at the positive electrode 112 to produce $C_2H_4$, $H^+$, and $e^-$ from $C_2H_6$; and additional elemental particles of a second metal discrete from the elemental particles of the first metal and formulated to accelerate reaction rates for the synthesis of higher hydrocarbons from the produced $C_2H_4$. In additional embodiments, the catalyst material of the positive electrode 112 comprises alloy particles individually including an alloy comprising the first metal and the second metal. In further embodiments, the catalyst material of the positive electrode 112 comprises composite particles including one of the first metal and the second metal partially (e.g., less than completely) coating (e.g., covering, encapsulating) the other of the first metal and the second metal, such as composite particles individually including a shell of the second metal partially coating a core of the first metal, and/or composite particles individually including a shell of the first metal partially coating a core of the second metal. In yet further embodiments, the catalyst material of the positive electrode 112 comprises composite particles including an alloy including one of the first metal and the second metal partially coating the another alloy including the other of the first metal and the second metal, such as composite particles individually including a shell of an alloy including the second metal partially coating a core of another alloy including the first metal, and/or composite particles individually including a shell of an alloy including the first metal partially coating a core of another alloy including the second metal. In still further embodiments, the catalyst material of the positive electrode 112 comprises composite particles including one of the first metal and the second metal partially coating an alloy including the other of the first metal and the second metal, such as composite particles individually including a shell of the second metal partially coating a core of an alloy including the first metal, and/or composite particles individually including a shell of the first metal partially coating a core of an alloy including the second metal. In yet still further embodiments, the catalyst material of the positive electrode 112 comprises composite particles including an alloy including one of the first metal and the second metal partially coating the other of the first metal and the second metal, such as composite particles individually including a shell of an alloy including the second metal partially coating a core of the first metal, and/or composite particles individually including a shell of an alloy including the first metal partially coating a core of the second metal.

As a non-limiting example, if the proton-conducting membrane 114 comprises a perovskite material (e.g., a BZCYYb, a BSNYYb, a doped $BaCeO_3$, a doped $BaZrO_3$, $Ba_2(YSn)O_{5.5}$, $Ba_3(CaNb_2)O_9$, etc.) having an operational temperature within a range of from about 350° C. to about 650° C., the positive electrode 112 may comprise a catalyst-doped perovskite material compatible with the perovskite material of the proton-conducting membrane 114. The positive electrode 112 may, for example, comprise a cermet material comprising at least one catalyst material including one or more (e.g., each) of nickel (Ni) and gold (Au), and at least one perovskite; such as one or more of a Ni/perovskite cermet (Ni-perovskite) material (e.g., Ni-BZCYYb, Ni-BSNYYb, Ni—$BaCeO_3$, Ni—$BaZrO_3$, Ni—$Ba_2(YSn)O_{5.5}$, Ni—$Ba_3(CaNb_2)O_9$) or a NiAu/perovskite cermet (NiAu-perovskite) material (e.g., NiAu-BZCYYb, NiAu-BSNYYb, NiAu—$BaCeO_3$, NiAu—$BaZrO_3$, NiAu—$Ba_2(YSn)O_{5.5}$, NiAu—$Ba_3(CaNb_2)O_9$. The catalyst material may include one or more of elemental particles individually including Ni or Au (e.g., Ni particles, Au particles), alloy particles individually including one or more (e.g., each) of Ni and Au (e.g., NiAu particles), and composite particles (e.g., core/shell particles) individually including one or more of Ni and Au (e.g., composite particles of Ni and Au). In some embodiments, the positive electrode 112 comprises Ni-BZCYYb. In additional embodiments, the positive electrode 112 comprises NiAu-BZCYYb.

As another non-limiting example, if the proton-conducting membrane 114 comprises a solid acid material (e.g., a doped $CsH_2PO_4$, an undoped $CsH_2PO_4$) having an operational temperature within a range of from about 200° C. to about 400° C., the positive electrode 112 may comprise a material (e.g., a catalytic alloy material) including one or more (e.g., each) Ni and Au (e.g., an NiAu alloy) that is compatible with the solid acid material of the proton-conducting membrane 114. In some embodiments wherein the proton-conducting membrane 114 comprises a solid acid material, the positive electrode 112 comprises an NiAu alloy.

As a further non-limiting example, if the proton-conducting membrane 114 comprises a PBI material (e.g., a doped PBI) having an operational temperature within a range of from about 150° C. to about 250° C., the positive electrode 112 may comprise one or more of at least one metal and at least one alloy (e.g., an NiAu alloy) compatible with the PBI material of the proton-conducting membrane 114. In some embodiments wherein the proton-conducting membrane 114 comprises a PBI material, the positive electrode 112 comprises an NiAu alloy.

Particles (e.g., elemental particles, alloy particles, composite particles) of the catalyst material of the catalyst-doped material of the positive electrode 112 may be nano-sized (e.g., individually having a cross-sectional width or diameter less than about one (1) µm, such as less than or equal to about 100 nanometers (nm), less than or equal to about 20 nm, or less than or equal to about 10 nm). In addition, the catalyst-doped material of the positive electrode 112 may exhibit any amount (e.g., concentration) and distribution of the catalyst material and any ratio of components thereof (e.g., any ratio of a first metal formulated to accelerate reaction rates at the positive electrode 112 to produce $C_2H_4$, $H^+$, and $e^-$ from $C_2H_6$ to a second metal formulated to accelerate reaction rates for the synthesis of higher hydrocarbons from the produced $C_2H_4$) facilitating desired non-oxidative $C_2H_6$ deprotonation reaction rates and desired ethyl coupling reaction rates at the positive electrode 112.

The catalyst-doped material of the negative electrode 116 includes at least one catalyst material thereon, thereover, and/or therein that accelerates reaction rates (e.g., nitrogen reduction reaction rates) at the negative electrode 116 to produce $NH_3$ from $N_2$, $H^+$, and $e^-$ in accordance with Equation (2) above. The catalyst material of the negative electrode 116 may, for example, comprise a metallic material (e.g., a metal, an alloy, a composite of two or more metals and/or alloys) formulated to accelerate reaction rates at the negative electrode 116 to produce $NH_3$ from $N_2$, $H^+$, and $e^-$.

The catalyst material of the negative electrode 116 may comprise a single (e.g., only one) element (e.g., a single metal), or may comprise multiple (e.g., more than one) elements (e.g., multiple metals). The catalyst material of the negative electrode 116 may comprise one or more of elemental particles, alloy particles, and composite particles. In some embodiments, the catalyst material of the negative electrode 116 comprises elemental particles of one or more metals formulated to accelerate reaction rates at the negative electrode 116 to produce $NH_3$ from $N_2$, $H^+$, and $e^-$. In additional embodiments, the catalyst material of the negative electrode 116 comprises alloy particles individually including an alloy comprising two or more metals, wherein at least one of the metals is formulated to accelerate reaction rates at the negative electrode 116 to produce $NH_3$ from $N_2$, $H^+$, and $e^-$. In further embodiments, the catalyst material of the negative electrode 116 comprises composite particles including a first metal and a second metal partially (e.g., less than completely) coating (e.g., covering, encapsulating) the first metal, (e.g., composite particles individually including a shell of the second metal partially coating a core of the first metal), wherein at least one of the metals is formulated to accelerate reaction rates at the negative electrode 116 to produce $NH_3$ from $N_2$, $H^+$, and $e^-$. In yet further embodiments, the catalyst material of the positive electrode 112 comprises composite particles including an alloy metal partially coating the another alloy, wherein at least one of the alloys includes a metal formulated to accelerate reaction rates at the negative electrode 116 to produce $NH_3$ from $N_2$, $H^+$, and $e^-$. In still further embodiments, the catalyst material of the negative electrode 116 comprises composite particles including an elemental metal partially coating an alloy, wherein at least one of the elemental metal and the alloy is formulated to accelerate reaction rates at the negative electrode 116 to produce $NH_3$ from $N_2$, $H^+$, and $e^-$. In yet still further embodiments, the catalyst material of the negative electrode 116 comprises composite particles including an alloy partially coating an elemental, wherein at least one of the alloy and the elemental metal is formulated to accelerate reaction rates at the negative electrode 116 to produce $NH_3$ from $N_2$, $H^+$, and $e^-$.

As a non-limiting example, if the proton-conducting membrane 114 comprises a perovskite material (e.g., a BZCYYb, a BSNYYb, a doped $BaCeO_3$, a doped $BaZrO_3$, $Ba_2(YSn)O_{5.5}$, $Ba_3(CaNb_2)O_9$, etc.) having an operational temperature within a range of from about 350° C. to about 650° C., the negative electrode 116 may comprise a catalyst-doped perovskite material compatible with the perovskite material of the proton-conducting membrane 114. The negative electrode 116 may, for example, comprise a cermet material comprising at least one catalyst material including one or more (e.g., each) of ruthenium (Ru) and an Ru alloy, and at least one perovskite; such as one or more of an Ru/perovskite cermet (Ru-perovskite) material (e.g., Ru-BZCYYb, Ru-BSNYYb, Ru—$PrBa_{0.5}Sr_{0.5}Co_{1.5}Fe_{0.5}O_{5+\delta}$ (Ru-PBSCF), Ru—$PrNi_{0.5}Co_{0.5}O_{3-\delta}$ (Ru-PNC), Ru—$Pr_{0.5}Ba_{0.5}Co_xFe_{1-x}O_3$, Ru—$Pr_{0.5}Ba_{0.5}FeO_3$, Ru—$BaCeO_3$, Ru—$BaZrO_3$, Ru—$Ba_2(YSn)O_{5.5}$, Ru—$Ba_3(CaNb_2)O_9$), an RuNi/perovskite cermet (RuNi-perovskite) material (e.g., RuNi-BZCYYb, RuNi-BSNYYb, RuNi-PBSCF, RuNi-PNC, RuNi—$Pr_{0.5}Ba_{0.5}Co_xFe_{1-x}O_3$, RuNi—$Pr_{0.5}Ba_{0.5}FeO_3$, RuNi—$BaCeO_3$, RuNi—$BaZrO_3$, RuNi—$Ba_2(YSn)O_{5.5}$, RuNi—$Ba_3(CaNb_2)O_9$), an RuCe/perovskite cermet (RuCe-perovskite) material (e.g., RuCe-BZCYYb, RuCe-BSNYYb, RuCe-PBSCF, RuCe-PNC, RuCe—$Pr_{0.5}Ba_{0.5}Co_xFe_{1-x}O_3$, RuCe—$Pr_{0.5}Ba_{0.5}FeO_3$, RuCe—$BaCeO_3$, RuCe—$BaZrO_3$, RuCe—$Ba_2(YSn)O_{5.5}$, RuCe—$Ba_3(CaNb_2)O_9$), and an RuNiCe/perovskite cermet (RuNiCe-perovskite) material (e.g., RuNiCe-BZCYYb, RuNiCe-BSNYYb, RuNiCe-PBSCF, RuNiCe-PNC, RuNiCe—$Pr_{0.5}Ba_{0.5}Co_xFe_{1-x}O_3$, RuNiCe—$Pr_{0.5}Ba_{0.5}FeO_3$, RuNiCe—$BaCeO_3$, RuNiCe—$BaZrO_3$, RuNiCe—$Ba_2(YSn)O_{5.5}$, RuNiCe—$Ba_3(CaNb_2)O_9$). The catalyst material may include one or more of elemental particles individually including Ru (e.g., Ru particles), alloy particles individually including Ru (e.g., RuCe particles, RuNi particles, RuNiCe particles), and composite particles (e.g., core/shell particles) individually including Ru (e.g., composite particles of Ru and Ni, composite particles of Ru and Ce, composite particles of Ru, Ni, and Ce). In some embodiments, the negative electrode 116 comprises RuNi-BZCYYb.

As another non-limiting example, if the proton-conducting membrane 114 comprises a solid acid material (e.g., a doped $CsH_2PO_4$, an undoped $CsH_2PO_4$) having an operational temperature within a range of from about 200° C. to about 400° C., the negative electrode 116 may comprise a material including Ru (e.g., elemental Ru, an Ru alloy) that is compatible with the solid acid material of the proton-conducting membrane 114. In some embodiments wherein the proton-conducting membrane 114 comprises a solid acid material, the negative electrode 116 comprises an RuNi alloy. In additional embodiments wherein the proton-conducting membrane 114 comprises a solid acid material, the negative electrode 116 comprises an RuCe alloy. In further embodiments wherein the proton-conducting membrane 114 comprises a solid acid material, the negative electrode 116 comprises an RuNiCe alloy. In yet further embodiments wherein the proton-conducting membrane 114 comprises a solid acid material, the negative electrode 116 comprises elemental Ru.

As a further non-limiting example, if the proton-conducting membrane 114 comprises a PBI material (e.g., a doped PBI) having an operational temperature within a range of from about 150° C. to about 250° C., the positive electrode 112 may comprise one or more of at least one metal and at least one alloy (e.g., an NiAu alloy) compatible with the PBI material of the proton-conducting membrane 114. In some embodiments wherein the proton-conducting membrane 114 comprises a PBI material, the negative electrode 116 comprises an RuNi alloy. In additional embodiments wherein the proton-conducting membrane 114 comprises a PBI material, the negative electrode 116 comprises an RuCe alloy. In further embodiments wherein the proton-conducting membrane 114 comprises a PBI material, the negative electrode 116 comprises an RuNiCe alloy. In yet further embodiments wherein the proton-conducting membrane 114 comprises a PBI material, the negative electrode 116 comprises elemental Ru.

Particles (e.g., elemental particles, alloy particles, composite particles) of the catalyst material of the catalyst-doped material of the negative electrode 116 may be nano-sized (e.g., individually having a cross-sectional width or diameter less than about one (1) μm, such as less than or equal to about 100 nm, less than or equal to about 20 nm, or less than or equal to about 10 nm). In addition, the catalyst-doped material of the negative electrode 116 may exhibit any amount (e.g., concentration) and distribution of the catalyst material and any ratio of components thereof facilitating desired nitrogen reduction reaction rates at the negative electrode 116.

The positive electrode 112 and the negative electrode 116 may each individually exhibit any desired dimensions (e.g., length, width, thickness) and any desired shape (e.g., a cubic shape, cuboidal shape, a tubular shape, a tubular spiral shape, a spherical shape, a semi-spherical shape, a cylindrical shape, a semi-cylindrical shape, a conical shape, a triangular prismatic shape, a truncated version of one or more of the foregoing, and irregular shape). The dimensions and the shapes of the positive electrode 112 and the negative electrode 116 may be selected relative to the dimensions and the shape of the proton-conducting membrane 114 such that the proton-conducting membrane 114 substantially intervenes between opposing surfaces of the positive electrode 112 and the negative electrode 116. Thicknesses of the positive electrode 112 and the negative electrode 116 may each individually be within a range of from about 10 μm to about 1000 μm.

The electrochemical cell 110, including the positive electrode 112, the proton-conducting membrane 114, and the negative electrode 116 thereof, may be formed through conventional processes (e.g., rolling process, milling processes, shaping processes, pressing processes, consolidation processes, etc.), which are not described in detail herein. The electrochemical cell 110 may be mono-faced or bi-faced and may have a prismatic, folded, wound, cylindrical, or jelly rolled configuration. The electrochemical cell 110 may be placed within the housing structure 108 to form the electrochemical apparatus 106, and may be electrically connected to the power source 118.

Although the electrochemical apparatus 106 is depicted as including a single (i.e., only one) electrochemical cell 110 in FIG. 1, the electrochemical apparatus 106 may include any number of electrochemical cells 110. Put another way, the electrochemical apparatus 106 may include a single (e.g., only one) electrochemical cell 110, or may include multiple (e.g., more than one) electrochemical cells 110. If the electrochemical apparatus 106 includes multiple electrochemical cells 110, each of the electrochemical cells 110 may be substantially the same (e.g., exhibit substantially the same components, component sizes, component shapes, component material compositions, component material distributions, component positions, component orientations, etc.) and may be operated under substantially the same conditions (e.g., substantially the same temperatures, pressures, flow rates, etc.), or at least one of the electrochemical cells 110 may be different (e.g., exhibit one or more of different components, different component sizes, different component shapes, different component material compositions, different component material distributions, different component positions, different component orientations, etc.) than at least one other of the electrochemical cells 110 and/or may be operated under different conditions (e.g., different temperatures, different pressures, different flow rates, etc.) than at least one other of the electrochemical cells 110. By way of non-limiting example, one of the electrochemical cells 110 may be configured for and operated under a different temperature (e.g., different operating temperature resulting from a different material composition of one of more components thereof, such as a different material composition of the proton-conducting membrane 114 thereof) than at least one other of the electrochemical cells 110. In some embodiments, two of more electrochemical cells 110 are provided in parallel with one another within the housing structure 108 of the electrochemical apparatus 106, and may individually produce a portion of the $N_2$ protonation products (e.g., $NH_3$) directed out of the electrochemical apparatus 106 as the $NH_3$ stream 126.

In addition, although the system 100 is depicted as including a single (i.e., only one) electrochemical apparatus 106 in FIG. 1, the system 100 may include any number of electrochemical apparatuses 106. Put another way, the system 100 may include a single (e.g., only one) electrochemical apparatus 106, or may include multiple (e.g., more than one) electrochemical apparatuses 106. If the system 100 includes multiple electrochemical apparatuses 106, each of the electrochemical apparatuses 106 may be substantially the same (e.g., exhibit substantially the same components, component sizes, component shapes, component material compositions, component material distributions, component positions, component orientations, etc.) and may be operated under substantially the same conditions (e.g., substantially the same temperatures, pressures, flow rates, etc.), or at least one of the electrochemical apparatus 106 may be different (e.g., exhibit one or more of different components, different component sizes, different component shapes, different component material compositions, different component material distributions, different component positions, different component orientations, etc.) than at least one other of the electrochemical apparatuses 106 and/or may be operated under different conditions (e.g., different temperatures, different pressures, different flow rates, etc.) than at least one other of the electrochemical apparatuses 106. By way of non-limiting example, one of the electrochemical apparatuses 106 may be configured for and operated under a different temperature (e.g., a different operating temperature resulting from a different material composition of one of more components of an electrochemical cell 110 thereof, such as a different material composition of the proton-conducting membrane 114 thereof) than at least one other of the electrochemical apparatuses 106. In some embodiments, two of more electrochemical apparatuses 106 are provided in parallel with one another. Each of the two of more electrochemical apparatuses 106 may individually receive a $C_2H_6$ stream 122 and a $N_2$ stream 124 and individually form an $NH_3$ stream 126 and a hydrocarbon product stream 128. In additional embodiments, two of more electrochemical apparatuses 106 are provided in series with one another.

Still referring to FIG. 1, the hydrocarbon product stream 124 and the $NH_3$ stream 126 exiting the electrochemical apparatus 106 may individually be utilized or disposed of as desired. In some embodiments, the hydrocarbon product stream 124 and the $NH_3$ stream 126 are individually delivered into one or more storage vessels for subsequent use, as desired. In additional embodiments, at least a portion of one or more of the hydrocarbon product stream 124 and the $NH_3$ stream 126 may be utilized (e.g., combusted) to heat one or more components (e.g., the heating apparatus 120 (if present); the electrochemical apparatus 106; etc.) and/or streams (e.g., the $C_2H_6$ stream 122, the $N_2$ stream 124) of the system 100. By way of non-limiting example, if the heating apparatus 120 (if present) is a combustion-based apparatus, at least a portion of one or more of the hydrocarbon product stream 124 and the $NH_3$ stream 126 may be directed into the heating apparatus 120 and undergo an combustion reaction to efficiently heat one or more of the $C_2H_6$ stream 122 entering the electrochemical apparatus 106, the $N_2$ stream 124 entering the electrochemical apparatus 106, and at least a portion of the electrochemical apparatus 106. Utilizing the hydrocarbon product stream 124 and/or the $NH_3$ stream 126 as described above may reduce the electrical power requirements of the system 100 by enabling the utilization of direct thermal energy.

Thermal energy input into (e.g., through the heating apparatus 120 (if present)) and/or generated by the electrochemical apparatus 106 may also be used to heat one or more other components and/or streams of the system 100. By way of non-limiting example, the hydrocarbon product stream 124 and/or the $NH_3$ stream 126 exiting the electrochemical apparatus 106 may be directed into a heat exchanger configured and operated to facilitate heat exchange between the hydrocarbon product stream 124 and/or the $NH_3$ stream 126 of the system 100 and one or more other relatively cooler streams (e.g., the $C_2H_6$ stream 122, the $N_2$ stream 124) of the system 100 to transfer heat from the hydrocarbon product stream 124 and/or the $NH_3$ stream 126 to the relatively cooler stream(s) to facilitate the recovery of the thermal energy input into and generated within the electrochemical apparatus 106. The recovered thermal energy may increase process efficiency and/or reduce operational costs without having to react (e.g., combust) higher hydrocarbon products of the hydrocarbon product stream 124 and/or $NH_3$ of the $NH_3$ stream 126.

The methods, systems (e.g., the system 100), and apparatuses (e.g., the electrochemical apparatus 106, including the electrochemical cell 110 thereof) of the disclosure facilitate the simple and efficient co-production of higher hydrocarbons (e.g., butylene, gasoline, diesel, etc.) and $NH_3$ from $C_2H_6$ at intermediate temperatures, such as temperatures within a range of from about 150° C. to about 600° C. The methods, systems, and apparatuses of the disclosure may reduce one or more of the time (e.g., processing steps), costs (e.g., material costs), and energy (e.g., thermal energy, electrical energy, etc.) required to produce higher hydrocarbons and $NH_3$ relative to conventional methods, systems, and apparatuses. The methods, systems, and apparatuses of the disclosure may be more efficient, durable, and reliable that conventional methods, conventional systems, and conventional apparatuses of producing higher hydrocarbons and $NH_3$.

While the disclosure is susceptible to various modifications and alternative forms, specific embodiments have been shown by way of example in the drawings and have been described in detail herein. However, the disclosure is not limited to the particular forms disclosed. Rather, the disclosure is to cover all modifications, equivalents, and alternatives falling within the scope of the following appended claims and their legal equivalent. For example, elements and features disclosed in relation to one embodiment may be combined with elements and features disclosed in relation to other embodiments of the disclosure.

What is claimed is:

1. A method of forming a hydrocarbon product and ammonia, comprising:
   introducing ethane ($C_2H_6$) to a positive electrode of an electrochemical cell comprising:
   the positive electrode;
   a negative electrode comprising one or more of a Ru/perovskite cermet, a RuNi/perovskite cermet, a RuCe/perovskite cermet, and a RuNiCe/perovskite cermet; and
   a proton-conducting membrane between the positive electrode and the negative electrode, the proton-conducting membrane comprising an electrolyte material having an ionic conductivity greater than or equal to about $10^{-2}$ S/cm at one or more temperatures within a range of from about 150° C. to about 600° C.;
   introducing $N_2$ to the negative electrode of the electrochemical cell; and
   applying a potential difference between the positive electrode and the negative electrode of the electrochemical cell while the $C_2H_6$ interacts with the positive electrode so that hydrogen (H) atoms of the $C_2H_6$ release electrons ($e^-$) to produce $C_2H_4$, hydrogen ions ($H^+$), and the $e^-$ at the positive electrode through non-oxidative deprotonation of the $C_2H_6$ at the one or more temperatures, to transport the $H^+$ through the proton-conducting membrane, and to produce $NH_3$ at the negative electrode.

2. The method of claim 1, further comprising selecting the proton-conducting membrane to comprise at least one perovskite material having a $H^+$ conductivity greater than or equal to about $10^{-2}$ S/cm at one or more temperatures within a range of from about 400° C. to about 600° C.

3. The method of claim 2, wherein selecting the proton-conducting membrane to comprise at least one perovskite material comprises selecting the at least one perovskite material to comprise one or more of a yttrium- and ytterbium-doped barium-zirconate-cerate (BZCYYb), a yttrium- and ytterbium-doped barium-strontium-niobate (BSNYYb), yttrium-doped $BaCeO_3$, yttrium-doped $BaZrO_3$, $Ba_2(YSn)O_{5.5}$, and $Ba_3(CaNb_2)O_9$.

4. The method of claim 1, further comprising selecting the proton-conducting membrane to comprise one or more of a yttrium- and ytterbium-doped barium-zirconate-cerate (BZCYYb), and a yttrium- and ytterbium-doped barium-strontium-niobate (BSNYYb).

5. The method of claim 1, further comprising selecting the proton-conducting membrane to comprise a yttrium- and ytterbium-doped barium-zirconate-cerate (BZCYYb).

6. The method of claim 1, further comprising selecting the proton-conducting membrane to comprise a yttrium- and ytterbium-doped barium-strontium-niobate (BSNYYb).

7. The method of claim 1, further comprising selecting the proton-conducting membrane to comprise $Ba_2(YSn)O_{5.5}$.

8. The method of claim 1, further comprising selecting the proton-conducting membrane to comprise $Ba_3(CaNb_2)O_9$.

9. The method of claim 1, further comprising selecting the negative electrode to comprise the Ru/perovskite cermet, the Ru/perovskite cermet selected from a Ru/yttrium- and ytterbium-doped barium-zirconate-cerate (Ru-BZCYYb) cermet and a Ru/yttrium- and ytterbium-doped barium-strontium-niobate (Ru-BSNYYb) cermet.

10. The method of claim 1, further comprising selecting the negative electrode to comprise the RuNi/perovskite cermet, the RuNi/perovskite cermet selected from a RuNi/yttrium- and ytterbium-doped barium-zirconate-cerate (RuNi-BZCYYb) cermet and a RuNi/yttrium- and ytterbium-doped barium-strontium-niobate (RuNi-BSNYYb) cermet.

11. The method of claim 10, wherein catalyst material of the RuNi/perovskite cermet comprises one or more of:
   RuNi alloy particles; and
   composite particles individually comprising:
      a core comprising one of Ru, Ni, and an RuNi alloy; and
      a shell partially coating the core and having a different material composition than the core, the shell comprising one other of the Ru, the Ni, and the RuNi alloy.

12. The method of claim 1, further comprising selecting the negative electrode to comprise the RuCe/perovskite cermet, the RuCe/perovskite cermet selected from a RuCe/yttrium- and ytterbium-doped barium-zirconate-cerate (RuCe-BZCYYb) cermet and a RuCe/yttrium- and ytterbium-doped barium-strontium-niobate (RuCe-BSNYYb) cermet.

13. The method of claim 12, wherein catalyst material of the RuCe/perovskite cermet comprises one or more of:
   RuCe alloy particles; and
   composite particles individually comprising:
      a core comprising one of Ru, Ce, and a RuCe alloy; and
      a shell partially coating the core and having a different material composition than the core, the shell comprising one other of the Ru, the Ce, and the RuCe alloy.

14. The method of claim 1, further comprising selecting the negative electrode to comprise the RuNiCe/perovskite cermet, the RuNiCe/perovskite cermet selected from a RuNiCe/yttrium- and ytterbium-doped barium-zirconate-cerate (RuNiCe-BZCYYb) cermet and a RuNiCe/yttrium- and ytterbium-doped barium-strontium-niobate (RuNiCe-BSNYYb) cermet.

15. The method of claim 14, wherein catalyst material of the RuNiCe/perovskite cermet comprises one or more of:
   RuNiCe alloy particles; and
   composite particles individually comprising Ru, Ni, and Ce.

\* \* \* \* \*

UNITED STATES PATENT AND TRADEMARK OFFICE
CERTIFICATE OF CORRECTION

| | | |
|---|---|---|
| PATENT NO. | : 11,731,920 B2 | |
| APPLICATION NO. | : 16/532276 | |
| DATED | : August 22, 2023 | |
| INVENTOR(S) | : Dong Ding et al. | |

Page 1 of 2

It is certified that error appears in the above-identified patent and that said Letters Patent is hereby corrected as shown below:

On the Title Page
In ITEM (57) ABSTRACT, Line 13, change "and NH3, and an" to --and $NH_3$, and an--

In the Specification

| | | |
|---|---|---|
| Column 1, | Line 17, | change "made government" to --made with government-- |
| Column 5, | Line 30, | change "electrode 112 (e.g." to --electrode 112 (e.g.,-- |
| Column 7, | Line 15, | change "streams 120 may" to --streams 122 may-- |
| Column 7, | Line 17, | change "streams 120 are" to --streams 122 are -- |
| Column 7, | Line 19, | change "streams 120 may" to --streams 122 may-- |
| Column 7, | Line 23, | change "streams exhibit" to --streams 122 may exhibit-- |
| Column 7, | Line 27, | change "streams 120." to --streams 122.-- |
| Column 7, | Line 41, | change "about 650°, the" to --about 650°), the-- |
| Column 9, | Lines 56-57, | change "$BaZr_{0.3}Ce_{0.5}Y_{0.1}O_{3-\delta}$);" to --$BaZr_{0.3}Ce_{0.5}Y_{0.1}Yb_{0.1}O_{3-\delta}$);-- |
| Column 11, | Line 29, | change "the $CH_4$ stream" to --the $C_2H_6$ stream-- |
| Column 11, | Line 32, | change "catalyst-doped materials of" to --catalyst-doped material of-- |
| Column 12, | Lines 47-48, | change "Ni—$BaCeO_3$, Ni—$BaZrO_3$, Ni—$Ba_2(YSn)O_{5.5}$, Ni—$Ba_3(CaNb_2)O_9$)" to --Ni-$BaCeO_3$, Ni-$BaZrO_3$, Ni-$Ba_2(YSn)O_{5.5}$, Ni-$Ba_3(CaNb_2)O_9$)-- |
| Column 12, | Lines 50-51, | change "NiAu—$BaCeO_3$, NiAu—$BaZrO_3$, NiAu—$Ba_2(YSn)O_{5.5}$, NiAu—$Ba_3(CaNb_2)O_9$." to --NiAu-$BaCeO_3$, NiAu-$BaZrO_3$, NiAu-$Ba_2(YSn)O_{5.5}$, NiAu-$Ba_3(CaNb_2)O_9$).-- |
| Column 14, | Lines 31-35, | change "Ru—$PrBa_{0.5}Sr_{0.5}Co_{1.5}Fe_{0.5}O_{5+\delta}$ (Ru-PBSCF), Ru—$PrNi_{0.5}Co_{0.5}O_{3-\delta}$ (Ru-PNC), Ru—$Pr_{0.5}Ba_{0.5}Co_xFe_{1-x}O_3$, Ru—$Pr_{0.5}Ba_{0.5}FeO_3$, Ru—$BaCeO_3$, Ru—$BaZrO_3$, Ru—$Ba_2(YSn)O_{5.5}$, Ru—$Ba_3(CaNb_2)O_9$)," to --Ru-$PrBa_{0.5}Sr_{0.5}Co_{1.5}Fe_{0.5}O_{5+\delta}$ (Ru-PBSCF), Ru- |

Signed and Sealed this
Fourteenth Day of May, 2024

Katherine Kelly Vidal
*Director of the United States Patent and Trademark Office*

CERTIFICATE OF CORRECTION (continued)
U.S. Pat. No. 11,731,920 B2

|  |  |  |
|---|---|---|
|  |  | $PrNi_{0.5}Co_{0.5}O_{3-\delta}$ (Ru-PNC), Ru- $Pr_{0.5}Ba_{0.5}Co_xFe_{1-x}O_3$, Ru-$Pr_{0.5}Ba_{0.5}FeO_3$, Ru-$BaZrO_3$, Ru-$Ba_2(YSn)O_{5.5}$, Ru-$Ba_3(CaNb_2)O_9$),-- |
| Column 14, | Lines 37-39, | change "RuNi—$Pr_{0.5}Ba_{0.5}Co_xFe_{1-x}O_3$, RuNi—$Pr_{0.5}Ba_{0.5}FeO_3$, RuNi—$BaCeO_3$, RuNi—$BaZrO_3$, RuNi—$Ba_2(YSn)O_{5.5}$, RuNi—$Ba_3(CaNb_2)O_9$)," to --RuNi- $Pr_{0.5}Ba_{0.5}Co_xFe_{1-x}O_3$, RuNi-$Pr_{0.5}Ba_{0.5}FeO_3$, RuNi-$BaCeO_3$, RuNi-$BaZrO_3$, RuNi-$Ba_2(YSn)O_{5.5}$, RuNi-$Ba_3(CaNb_2)O_9$),-- |
| Column 14, | Lines 41-43, | change "RuCe—$Pr_{0.5}Ba_{0.5}Co_xFe_{1-x}O_3$, RuCe—$Pr_{0.5}Ba_{0.5}FeO_3$, RuCe—$BaCeO_3$, RuCe—$BaZrO_3$, RuCe—$Ba_2(YSn)O_{5.5}$, RuCe—$Ba_3$" to --RuCe-$Pr_{0.5}Ba_{0.5}Co_xFe_{1-x}O_3$, RuCe-$Pr_{0.5}Ba_{0.5}FeO_3$, RuCe-$BaCeO_3$, RuCe-$BaZrO_3$, RuCe-$Ba_2(YSn)O_{5.5}$, RuCe-$Ba_3$-- |
| Column 14, | Lines 46-49, | change "RuNiCe—$Pr_{0.5}Ba_{0.5}Co_xFe_{1-x}O_3$, RuNiCe—$Pr_{0.5}Ba_{0.5}FeO_3$, RuNiCe—$BaCeO_3$, RuNiCe—$BaZrO_3$, RuNiCe—$Ba_2(YSn)O_{5.5}$, RuNiCe—$Ba_3(CaNb_2)O_9$)." to --RuNiCe-$Pr_{0.5}Ba_{0.5}Co_xFe_{1-x}O_3$, RuNiCe-$Pr_{0.5}Ba_{0.5}FeO_3$, RuNiCe-$BaCeO_3$, RuNiCe-$BaZrO_3$, RuNiCe-$Ba_2(YSn)O_{5.5}$, RuNiCe-$Ba_3(CaNb_2)O_9$).-- |
| Column 16, | Line 36, | change "two of more" to --two or more-- |
| Column 17, | Line 16, | change "124 and the" to --128 and the-- |
| Column 17, | Line 19, | change "stream 124 and" to --stream 128 and-- |
| Column 17, | Line 22, | change "stream 124 and" to --stream 128 and-- |
| Column 17, | Line 30, | change "stream 124 and" to --stream 128 and-- |
| Column 17, | Line 36, | change "stream 124 and/or" to --stream 128 and/or-- |
| Column 17, | Line 45, | change "stream 124 and/or" to --stream 128 and/or-- |
| Column 17, | Line 48, | change "product stream 124" to --product stream 128-- |
| Column 17, | Line 52, | change "stream 124 and/or" to --stream 128 and/or-- |
| Column 17, | Line 59, | change "stream 124 and/or" to --stream 128 and/or-- |